US010150002B2

(12) United States Patent
Kass et al.

(10) Patent No.: US 10,150,002 B2
(45) Date of Patent: Dec. 11, 2018

(54) HEALTH TRACKING DEVICES

(71) Applicant: Accenture Global Solutions Limited, Dublin (IE)

(72) Inventors: Alex M. Kass, Palo Alto, CA (US); Dadong Wan, San Jose, CA (US)

(73) Assignee: Accenture Global Solutions Limited, Dublin (IE)

( * ) Notice: Subject to any disclaimer, the term of this patent is extended or adjusted under 35 U.S.C. 154(b) by 233 days.

(21) Appl. No.: 15/040,690

(22) Filed: Feb. 10, 2016

(65) Prior Publication Data

US 2017/0225034 A1    Aug. 10, 2017

(51) Int. Cl.
*A63B 24/00* (2006.01)
*A63B 21/00* (2006.01)
*A63B 22/00* (2006.01)
*G09B 19/00* (2006.01)

(52) U.S. Cl.
CPC .......... *A63B 24/0062* (2013.01); *A63B 21/00* (2013.01); *A63B 22/00* (2013.01); *A63B 24/0075* (2013.01); *A63B 24/0087* (2013.01); *G09B 19/00* (2013.01)

(58) Field of Classification Search
CPC ............ A63B 24/0062; A63B 24/0065; A63B 24/0068; A63B 24/0071; A63B 24/0078; A63B 24/0081; A63B 24/0087; A63B 24/0075; A63B 5/0022; A63B 5/0205; G06F 19/3418; G06F 19/3481
See application file for complete search history.

(56) References Cited

U.S. PATENT DOCUMENTS

| 5,738,612 | A | * | 4/1998 | Tsuda | A61B 5/02225 482/5 |
| 7,970,620 | B2 | | 6/2011 | Brown | |
| 9,215,979 | B2 | | 12/2015 | Brown | |
| 2001/0041647 | A1 | * | 11/2001 | Itoh | A63B 22/00 482/9 |
| 2004/0122486 | A1 | | 6/2004 | Stahmann et al. | |
| 2007/0219059 | A1 | * | 9/2007 | Schwartz | A61B 5/0205 482/8 |
| 2010/0009810 | A1 | * | 1/2010 | Trzecieski | A63B 24/0062 482/8 |
| 2011/0082007 | A1 | * | 4/2011 | Birrell | A63B 24/0059 482/8 |

(Continued)

*Primary Examiner* — Milap Shah
(74) *Attorney, Agent, or Firm* — Fish & Richardson P.C.

(57) ABSTRACT

Methods, systems, and apparatus, including computer programs encoded on a computer storage medium, for promoting healthy behavior. The methods, systems, and apparatus include an action of receiving device capability information for multiple devices. The device capability information from each device describes capabilities of the device. Additional actions include receiving an indication of a health goal of a user and receiving health information of the user sensed by a first device of the multiple devices. Further actions include generating a health related instruction for a second device of the multiple devices based on the health information of the user sensed by the first device of the multiple devices, the health goal of the user, and the device capability information of the second device. An additional action includes providing the health related instruction to the second device.

20 Claims, 3 Drawing Sheets

(56) References Cited

U.S. PATENT DOCUMENTS

| | | | |
|---|---|---|---|
| 2011/0086707 A1* | 4/2011 | Loveland | A63B 24/0087 463/36 |
| 2013/0225370 A1* | 8/2013 | Flynt | A63B 24/0087 482/4 |
| 2014/0135173 A1* | 5/2014 | Watterson | A63B 24/0087 482/8 |

* cited by examiner

HEALTH TRACKING DEVICES

TECHNICAL FIELD

This disclosure generally relates to health tracking devices.

BACKGROUND

Various devices are in existence that sense health information of users. For example, wearable devices may measure a number of steps that a person takes, electronic scales may measure a weight of a person, and exercise equipment may track an amount of exercise that a person engages in using the exercise equipment.

SUMMARY

In general, an aspect of the subject matter described in this specification may involve enhancements to health tracking devices which may promote healthy behavior. Devices may sense health information of a user. For example, a wearable device may measure a number of steps that a user takes and provide a user a report of the number of steps that a user has taken. However, these devices typically do not respond to health information for a user received from other devices. In a healthy behavior promotion platform, various devices may register with a healthy behavior promotion engine. In registering, the various devices may provide capability information that describes the device's capabilities. The engine may further receive a health goal of a user and sensed health information for the user from a device that is registered with the engine. The engine may then generate an instruction for another registered device to act on for promoting healthy behavior of the user. For example, the instruction may be for the other registered device to display a recommendation to the user for performing a particular healthy behavior or for the other registered device to change the type of health information of the user that the device senses. Accordingly, the health information sensed by one registered device, health goal of a user, and previously provided capability of another registered device may be used to generate instructions for the other registered device.

In some aspects, the subject matter described in this specification may be embodied in methods that may include the action of receiving device capability information for multiple devices. The device capability information from each device describes capabilities of the device. Additional actions include receiving an indication of a health goal of a user and receiving health information of the user sensed by a first device of the multiple devices. Further actions include generating a health related instruction for a second device of the multiple devices based on the health information of the user sensed by the first device of the multiple devices, the health goal of the user, and the device capability information of the second device. An additional action includes providing the health related instruction to the second device.

Other versions include corresponding systems, apparatus, and computer programs, configured to perform the actions of the methods, encoded on computer storage devices.

These and other versions may each optionally include one or more of the following features. For instance, in some implementations the first device is a wearable device. In certain aspects, the second device is an exercise device. In some aspects, the health related instruction causes the second device to change a behavior of the second device. In some implementations, the health related instruction causes the second device to display a recommendation of a particular exercise for the user. In certain aspects, the health related instruction causes the second device to begin monitoring particular health information of the user. In some aspects, receiving an indication of a health goal of a user includes receiving the indication of the health goal of the user from a health provider device.

In some implementations, generating a health related instruction for a second device of the multiple devices based on the health information of the user sensed by the first device of the multiple devices, the health goal of the user, and the device capability information of the second device includes determining a health model that matches the health goal of the user, identifying one or more user behaviors based on the health model and the health information of the user, selecting a user behavior that is enabled by a capability of the second device indicated by the device capability information of the second device, and determining the health related instruction for the second device based on the selected user behavior.

The details of one or more implementations of the subject matter described in this specification are set forth in the accompanying drawings and the description below. Other potential features, aspects, and advantages of the subject matter will become apparent from the description, the drawings, and the claims.

DESCRIPTION OF DRAWINGS

Like reference symbols in the various drawings indicate like elements.

DETAILED DESCRIPTION

Figure 1:
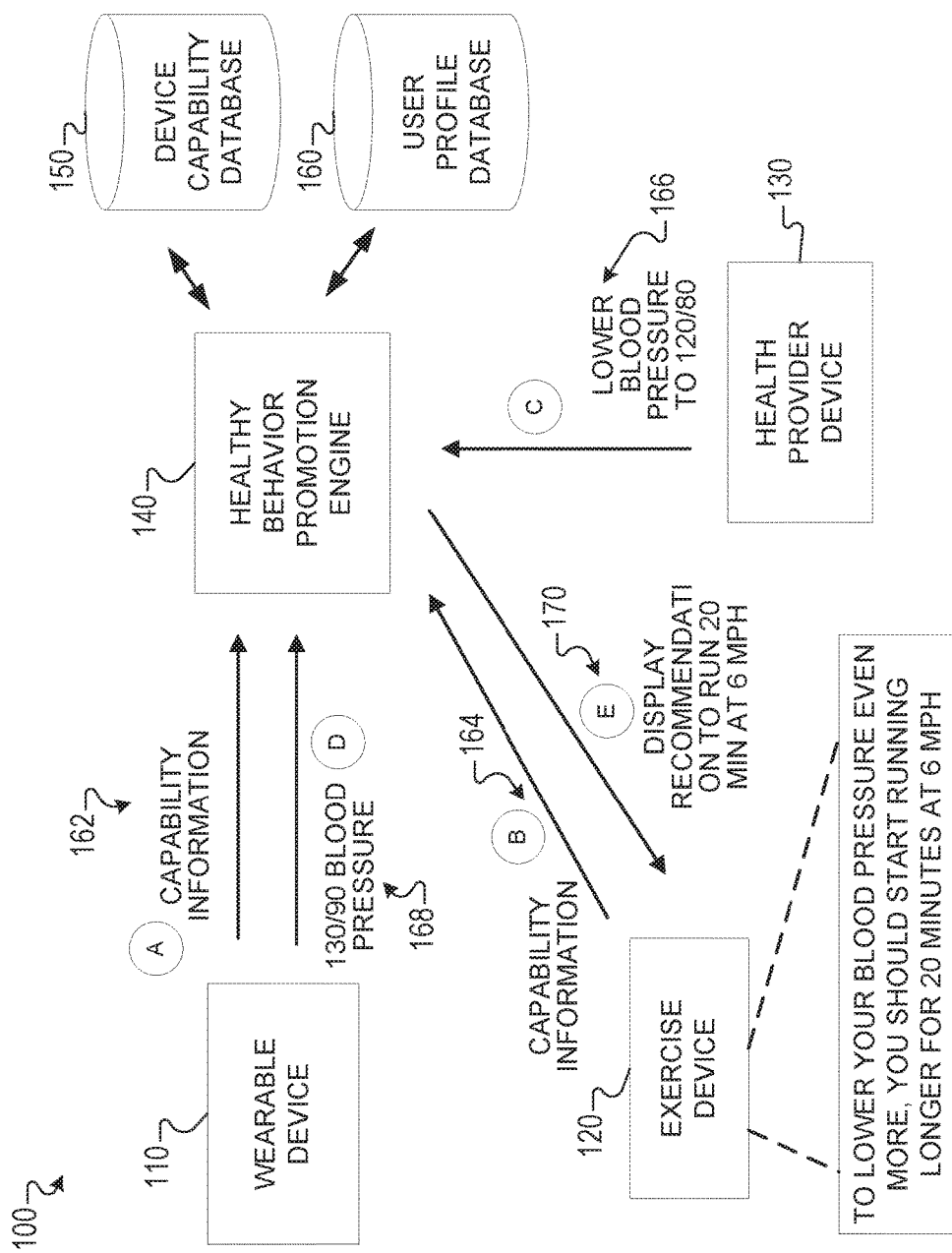
FIG. 1 is a block diagram of an example system for promoting healthy behavior.

FIG. 1 is a block diagram of an example system 100 for promoting healthy behavior. The system 100 includes a wearable device 110 worn by a user, an exercise device 120 used by the user, a health provider device 130 that indicates a health goal of a user, a healthy behavior promotion engine 140 that generates instructions that promote healthy behavior, a device capability database 150 that stores capability information of devices, and a user profile database 160 that stores profiles of users.

The wearable device 110 may be a device worn by a user that senses health information of the user. For example, the wearable device 110 may be a device that is worn by the user that senses a number of steps a user takes, measures a blood pressure of the user, measures a heart rate of the user, measures a glucose level of the user, or senses some other health related information of a user. The wearable device 110 may transmit the sensed health information to the engine 140. For example, the wearable device 110 may transmit data indicating that the user's current blood pressure is 130/90.

The wearable device 110 may change its behavior. For example, the wearable device 110 may enable or disable monitoring functionality, e.g., enable or disable monitoring one or more of a blood pressure of a user and a number of steps of a user. The wearable device 110 may change its behavior based on instructions from the engine 140. For example, when the wearable device 110 is already monitoring a number of steps of a user, the wearable device 110 may receive instructions from the engine 140 to also monitor a blood pressure of a user and in response, change from monitoring a number of steps of a user to also monitoring a blood pressure of the user. In another example, the wearable device 110 may receive instructions from the engine 140 to begin monitoring a location of the user and in response, turn on a global positioning system sensor in the wearable device 110.

The wearable device 110 may register with the engine 140 by providing capability information to the engine 140. The capability information may describe the functions of the wearable device 110 that may be enabled or disabled. For example, the wearable device 110 may provide the engine 140 capability information that indicates that the wearable device 110 is capable of monitoring a blood pressure of a user and the number of steps that a user takes. The wearable device 110 may provide the capability information in response to the engine 140 requesting capability information from the wearable device 110 or in response to input from the user requesting that the wearable device 110 register with the engine 140. In some implementations, the wearable device 110 may also provide information to the engine 140 indicating inputs that the wearable device 110 may receive from the engine 140 and outputs that the wearable device 110 may provide the engine 140.

The wearable device 110 may additionally or alternatively be registered with a user. For example, a user may enable the wearable device 110 to share information about the user by entering user profile credentials for the profile associated with the user on the system 100 and indicating that the wearable device 110 may continue to share about the user until (i) the user explicitly indicates that the wearable device 110 should stop sharing information, (ii) a predetermined length of time has elapsed, or (iii) some other condition has been satisfied.

The exercise device 120 may be another device that senses health information of the user. For example, the exercise device 120 may be a treadmill that senses a user's running speed, running time, and incline based on settings of the treadmill. The exercise device 120 may provide the sensed health information of the user to the engine 140. For example, the exercise device 120 may transmit the user's running speed, running time, and incline on the exercise device 120 to the engine 140. In some implementations, the exercise device 120 may transmit information to the engine 140 that indicates that the exercise device 120 is about to be used by the user. For example, the exercise device 120 may transmit information that indicates that the user has turned on the exercise device 120 or has identified himself or herself to the exercise device 120.

The exercise device 120 may change its behavior. For example, the exercise device 120 may increase or decrease in speed or incline, or display prompts or recommendations to a user. The exercise device 120 may change its behavior based on instructions from the engine 140. For example, the exercise device 120 may receive instructions from the engine 140 to display a recommendation that a user run twenty minutes at six miles per hour, and in response, display the recommendation.

The exercise device 120 may register with the engine 140 by providing capability information to the engine 140. For example, the exercise device 120 may provide the engine 140 capability information that indicates that the exercise device 120 is capable of operating at a speed between zero and fifteen miles per hour and an incline of zero to fifteen degrees. The exercise device 120 may provide the capability information in response to the engine 140 requesting capability information from the exercise device 120 or in response to input from the user requesting that the exercise device 120 register with the engine 140. In some implementations, the exercise device 120 may also provide information to the engine 140 indicating inputs that the exercise device 120 may receive from the engine 140 and outputs that the exercise device 120 may provide the engine 140.

The exercise device 120 may additionally or alternatively be registered with a user. For example, in the case of a user owned exercise device, a user may enable the exercise device 120 to share information about the user by entering user profile credentials for the profile associated with the user on the system 100 and indicating that the exercise device 120 may continue to share information about the user until (i) the user explicitly indicates that the exercise device 120 should stop sharing information, (ii) a predetermined length of time has elapsed, or (iii) some other condition has been satisfied. In another example, in the case of a community owned exercise device, e.g., an exercise bike at a gym, the exercise device 120 may provide user profile credentials to authorize the exercise device to associate information with the user's profile and share the information about the user, and may provide a user interface for the user to designate when the exercise device 120 should begin sharing information and stop sharing information.

The health provider device 130 may be a device that provides the engine 140 an indication of a health goal of the user. For example, the health provider device 130 may be a server of a doctor's office that is in communication with the engine 140 and provides an indication to the engine 140 that a doctor and user have agreed on a health goal for the user of lowering the user's blood pressure to 120/80. Other health goals may include, for example, increasing strength in a particular group of muscles, increasing flexibility, increasing endurance, losing weight, or other goals related to a user's health. In some implementations, the health provider device 130 may also provide information to the engine 140 indicating inputs that the health provider device 130 may receive from the engine 140 and outputs that the health provider device 130 may provide the engine 140. The health provider device 130 may additionally or alternatively be registered with a user. For example, while at a doctor's office, a user may input user profile credentials for a user's profile and indicate that the health provider device 130 may receive and share information about the user until (i) the user provides subsequent user input to end the sharing, (ii) the appointment time for the user has elapsed, or (iii) some other condition has been satisfied.

The engine 140 may provide instructions for devices based on information sensed by the devices, capability information of the devices, and a health goal of the user. For example, the engine 140 may provide an instruction to the exercise device 120 to display a recommendation to the user to run twenty minutes at six miles per hour based on information indicating that (i) user's current blood pressure is 130/90, (ii) the user is using the exercise device 120 that is capable of speeds between zero and fifteen miles per hour and an incline of zero to fifteen degrees, and (iii) has a goal of reaching a blood pressure of 120/80.

The engine 140 may receive capability information from the devices (162, 164). For example, in a registration process the engine 140 may receive over a network, e.g., the Internet, capability information from wearable device 110 indicating that the wearable device 110 is capable of monitoring a blood pressure of a user and the number of steps that a user takes and receive capability information from exercise device 120 indicating the exercise device 120 is capable of speeds between zero and fifteen miles per hour and an incline of zero to fifteen degrees. The engine 140 may store the capability information in the device capability database 150. For example, the engine 140 may store, for later access, information indicating that the exercise device 120 is capable of speeds between zero and fifteen miles per hour and an incline of zero to fifteen degrees in the device capability database 150.

The engine 140 may receive an indication of a health goal of the user (166). For example, the engine 140 may, from the health provider device 130, receive an indication that a health goal of the user is reaching a blood pressure of 120/80. The engine 140 may store the indication of the health goal of the user in the user profile database 160. For example, the engine 140 may store, for later access, information indicating that a user's goal is reaching a blood pressure of 120/80.

The engine 140 may receive health information of the user sensed by devices (168). For example, the engine 140 may receive health information from the wearable device 110 that indicates that the user's current blood pressure is 130/90. In another example, the engine 140 may receive health information from the wearable device 110 that indicates that the user has taken one thousand steps that day. In some implementations, the engine 140 may apply translation functions to translate health information that is received from a device into a common or unified vocabulary based on the registration information from devices that indicates the type of outputs that the device provides. For example, the engine 140 may receive information from an exercise device that indicates that the exercise device provides output regarding a distance run in meters and, in response, identify and apply a translation function for converting meters to miles. In another example, the engine 140 may receive information from a wearable device that indicates that the wearable device provides output on heart rate in the form of beats per five minutes and, in response, identify and apply a translation function for converting beats per five minutes to beats per minute.

The engine 140 may generate an instruction for a device based on the health information, the capability information, and the health goal of the user. For example, the engine 140 may receive an indication from the exercise device 120 that the user is about to start exercising on the exercise device 120, and in response, determine that a user's goal is reducing their blood pressure to 120/80, determine that from a current blood pressure of 130/90 that long aerobic activities are generally more effective than short strength related activities, determine from the exercise device's capability information that a long aerobic activity available through the exercise device 120 is a run for twenty minutes at six miles per hour, and determine that the instruction for the exercise device 120 is to recommend to the user that the user run for twenty minutes at six miles per hour.

In another example, the engine 140 may regularly update an instruction for the exercise device 120 and other devices in response to health information received from devices, and in response to an indication from the exercise device 120 indicating that the user is about to use the exercise device 120, provide the current instruction for the exercise device 120 that was determined before the indication was received from the exercise device 120.

In other examples, different instructions may be provided to the exercise device 120. For example, the engine 140 may determine that the exercise device 120 is capable of determining an effective exercise routine for the user based on a blood pressure goal and a current blood pressure of the user, and in response, determine to transmit an instruction to the exercise device 120 indicating the blood pressure goal, the current blood pressure of the user to the exercise device 120, and that the exercise device 120 should determine an effective exercise routine. In yet another example, the engine 140 may determine that a health goal of the user is to lose weight and in response to sensed information from the wearable device 110 that indicates a number of steps that a user has taken, determine an amount of time, speed, and incline at which the user should run to lose weight.

In some implementations, the engine 140 may generate the instructions for a device based on registration information from the device describing inputs the device can receive. For example, the engine 140 may determine an instruction in a common or unified vocabulary, identify a translation function for the device to translate a common or unified vocabulary to an input usable by the device, and apply the translation function to the instruction in the common or unified vocabulary.

The engine 140 may transmit the instruction to the exercise device 120. For example, the engine 140 may transmit an instruction that the exercise device 120 display a recommendation that the user run for twenty minutes at six miles per hour, and in response, the exercise device 120 may display to the user, "To lower your blood pressure event more, you should start running longer for twenty minutes at six miles per hour."

In some implementations, the engine 140 may determine instructions based on health related models. For example, the engine 140 may determine instructions for reaching a goal based on a health related model reflecting an impact of different types of user behavior on reaching the goal. The engine 140 may generate the health related models. For example, the engine 140 may store user behavior and sensed health information of other users to determine activities or exercises that resulted in sensed health related information that indicates that the user engaging in the behavior would help the user progress towards the user's health goal. Accordingly, the engine 140 may determine a health related model that is classified as matching the health goal of the user, determine user behaviors that help the user reach their health goal based on the health related model and the health information, determine, based on the capability information for the device, a behavior that a device is capable of enabling that would result in the user engaging in one or more of the user behaviors determined to help the user reach their health goal, and provide a health related instruction to the device for the device to change its behavior to the determined behavior that would result in the user engaging in one or more of the user behaviors determined to help the user reach their health goal.

In some implementations, the engine 140 may additionally or alternatively determine instructions based on (i) behavioral information, e.g., kinds of exercise that a user does, type of diet that the user follows, amount of time the user spent relaxing versus working, or sitting versus standing versus reclining, or other behaviors, (ii) the health information, e.g., metabolic, temperature, glucose level, or other health information, and (iii) environmental condition information, e.g., noise level, smoke level in air, freshness of air, ambient temperature, or other environmental conditions. For example, the engine 140 may determine from behavioral information that the only cardiovascular activity that the user engages in is running, that the user's heart rate is moderately high, and that the freshness of air is high, and in response, determine that the user should run longer and at a higher incline on the exercise device 120 than if the freshness of the air quality was lower or than if the user engaged in other cardiovascular activities besides running.

The engine 140 may obtain the behavioral information based on user input that explicitly provides the behavioral information, e.g., a user indicating kinds of exercises that the user performs or based on other input, e.g., the engine 140 determining what exercises the user performs based identifying exercises associated with exercise devices that the user authorizes to share information about the user or identifying exercises associated with types of movements indicated by the wearable device 110. The engine 140 may obtain the environmental condition information from sensors, e.g., a mobile device of the user indicating an amount of ambient noise or an air quality sensor indicating a smoke level in air, or from user input, e.g., a user providing input on ambient temperature through a mobile device.

In some implementations, the engine 140 may additionally or alternatively suggest behavioral or environmental changes based on one or more the behavioral information, the health information, or the environmental condition information. For example, the engine 140 may determine from the health information from a wearable device when a user sleeps, determine from a mobile device of the user that it is noisy when the user sleeps, and determine from behavioral information that the user does not sleep enough, and in response, provide a suggestion to sleep more, a suggestion to reduce an amount of noise when the user sleeps, a suggestion to reduce an ambient temperature when the user sleeps, or some other suggestion that may result in the user sleeping more.

In the system 100, additional or other devices may be used with the engine 140. For example, the exercise device 120 or the wearable device 110 may be a stair climber device, a row machine, or some other device that provides capability information to the engine 140, changes a behavior based on instructions received from the engine 140, and provides sensed health information to the engine 140. In another example, the system 100 may include a stair climber or a row machine in addition to a treadmill.

Figure 2:
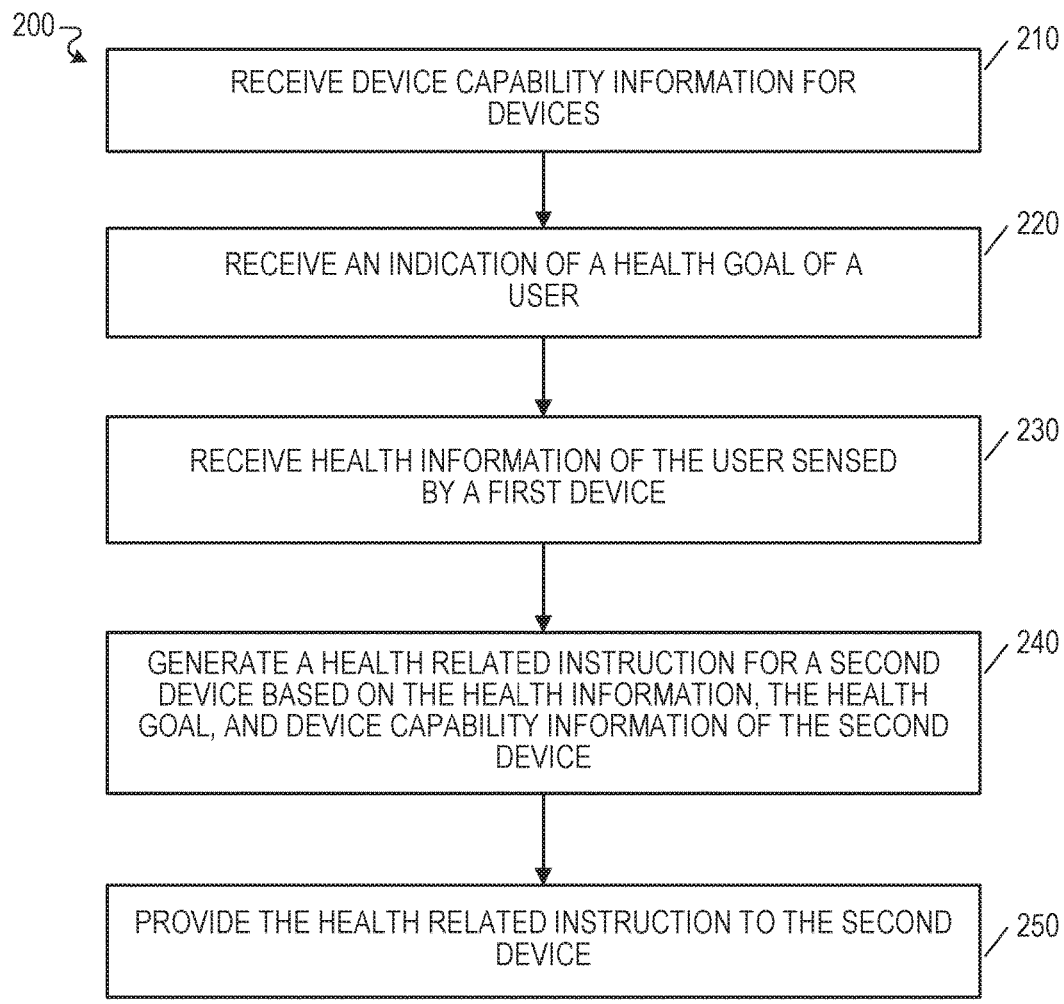
FIG. 2 is a flowchart of an example process for promoting healthy behavior.

FIG. 2 is a flowchart of an example process 200 for promoting healthy behavior. The following describes the process 200 as being performed by components of the system 100 that are described with reference to FIG. 1. However, the process 200 may be performed by other systems or system configurations.

The process 200 may include receiving device capability information for devices (210). For example, the health behavior promotion engine 140 may receive, over a network, capability information from the wearable device 110 indicating that the wearable device 110 is capable of monitoring arm movements of a user and a heart rate of the user, and receive capability information from the exercise device 120 that indicates that the exercise device 120 is a row machine capable of adjusting a resistance of rowing. The device capability information for the devices may be received in response to the health behavior promotion engine 140 requesting device capability information or a device initiating a registration with the health behavior promotion engine 140.

The process 200 may include receiving an indication of a health goal of a user (220). For example, the health behavior promotion engine 140 may receive, over a network from the health provider device 130, an indication that a user's health goal is to reduce a resting heart rate of a user to less than fifty beats a minute.

The process 200 may include receiving health information of the user sensed by a first device (230). For example, the health behavior promotion engine 140 may receive, over a network from the wearable device 110, health information that indicates that a user's current heart rate is sixty five beats a minute and the user is making one row motion every three seconds.

The process 200 may include generating a health related instruction for a second device based on the health information, the health goal, and device capability information of the second device (240). For example, the health behavior promotion engine 140 may determine that based on the heart rate of sixty five beats a minute and the user making one row motion every three seconds that a user's work out should be more intense to reach the user's health goal of a resting heart rate of less than fifty beats a minute, determine from the device capability that the user's workout may be made more intense by increasing a resistance of the exercise device 120, and in response, generating a health related instruction for the exercise device 120 to increase a resistance.

The process 200 may include providing the health related instruction to the second device (250). For example, the health behavior promotion engine 140 may provide the exercise device 120 an instruction to increase a resistance.

Figure 3:
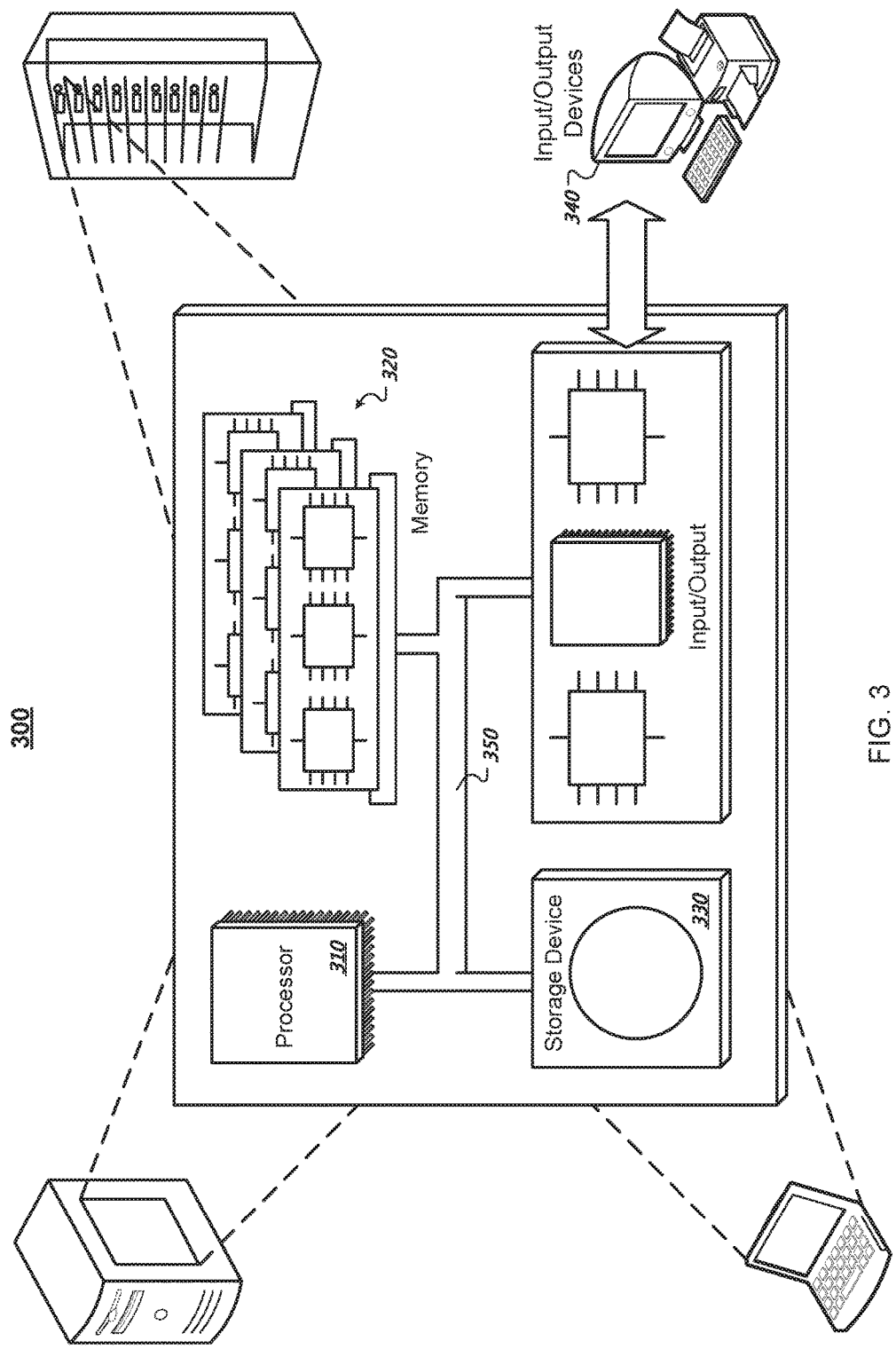
FIG. 3 illustrates a schematic diagram of an exemplary computer system.

FIG. 3 illustrates a schematic diagram of an exemplary computer system. The system 300 can be used for the operations described in association with the processes 200 according to some implementations. The system 300 may be included in the system 100.

The system 300 includes a processor 310, a memory 320, a storage device 330, and an input/output device 340. Each of the components 310, 320, 330, and 320 are interconnected using a system bus 350. The processor 310 is capable of processing instructions for execution within the system 300. In one implementation, the processor 310 is a single-threaded processor. In another implementation, the processor 310 is a multi-threaded processor. The processor 310 is capable of processing instructions stored in the memory 320 or on the storage device 330 to display graphical information for a user interface on the input/output device 340.

The memory 320 stores information within the system 300. In one implementation, the memory 320 is a computer-readable medium. In one implementation, the memory 320 is a volatile memory unit. In another implementation, the memory 320 is a non-volatile memory unit.

The storage device 330 is capable of providing mass storage for the system 800. In one implementation, the storage device 330 is a computer-readable medium. In various different implementations, the storage device 330 may be a floppy disk device, a hard disk device, an optical disk device, or a tape device.

The input/output device 340 provides input/output operations for the system 800. In one implementation, the input/output device 340 includes a keyboard and/or pointing device. In another implementation, the input/output device 340 includes a display unit for displaying graphical user interfaces.

Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them. In some cases, the one or more programmable computers may be connected by a network to form a distributed computing environment (e.g., a cloud).

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The invention claimed is:

1. A computer-implemented method comprising:
receiving, at a server of a system that includes (i) the server and (ii) a set of multiple devices that include a wearable device and an exercise machine, device capability information for each device in the set of multiple devices, where the device capability information from each device describes capabilities of the device and the exercise machine is configured to be triggerable by the server to perform a physical action that makes a long aerobic physical activity available to the user;
receiving, by the server, an indication of a health goal of a user;
receiving, by the server, heart rate information of the user sensed by the wearable device of the multiple devices;
determining, by the server based on the heart rate information sensed by the wearable sensor and the health goal of the user, to provide the long aerobic physical activity for the user to perform instead of to provide a short strength related physical activity for the user to perform;
determining, by the server, from the device capability information from the exercise machine that the long aerobic physical activity is available through the exercise device with performance of a physical action by the exercise machine;
in response to determining from the device capability information from the exercise machine that the long aerobic physical activity is available through the exercise machine with performance of the physical action by the exercise machine, generating, by the server, a health related instruction that triggers the exercise machine of the multiple devices to perform the physical action that makes the long aerobic physical activity available to the user;
receiving, by the server, an indication that the user has turned on the exercise machine; and
in response to receiving the indication that the user has turned on the exercise machine, providing, by the server to the exercise machine, the health related instruction that triggers the exercise machine to perform the physical action that makes the long aerobic physical activity available to the user.

2. The method of claim 1, wherein the health related instruction additionally causes the exercise machine to display a recommendation of a particular exercise for the user.

3. The method of claim 1, wherein health related instruction additionally causes the exercise machine to begin monitoring particular health information of the user.

4. The method of claim 1, wherein receiving an indication of a health goal of a user comprises:
receiving the indication of the health goal of the user from a health provider device.

5. The method of claim 1, wherein generating, a health related instruction that triggers the exercise machine of the multiple devices to perform the physical action that makes the long aerobic physical activity available to the user comprises:
determining a health model that matches the health goal of the user;
identifying one or more user behaviors based on the health model and the health information of the user;
selecting a user behavior that is enabled by a capability of the exercise machine indicated by the device capability information of the exercise machine; and
determining the health related instruction for the exercise machine based on the selected user behavior.

6. The method of claim 1, wherein receiving device capability information comprises:
providing a first request for capability information to the wearable device;
receiving device capability information from the wearable device in response to the first request;
providing a second request for capability information to the exercise machine; and
receiving device capability information from the exercise machine in response to the second request.

7. The method of claim 1, wherein the exercise machine comprises a treadmill, a row machine, or a stair climber device.

8. The method of claim 1, wherein receiving device capability information comprises receiving, from a treadmill, an indication of a range of speeds that the treadmill is capable of operating between,
wherein generating a health related instruction that triggers the exercise machine of the multiple devices to perform a physical action comprises determining, based at least on (i) the health goal of the user, (ii) the range of speeds that the treadmill is capable of operating between, and (iii) the heart rate information sensed by the wearable device, a speed that the treadmill should operate at between the range of speeds that the treadmill is capable of operating between.

9. The method of claim 1, wherein generating, a health related instruction that triggers the exercise machine of the multiple devices to perform the physical action comprises:
obtaining the heart rate information;
translating the heart rate information into a unified vocabulary using a first translation function;
generating the health related instruction in the unified vocabulary based at least on the heart rate information translated into the unified vocabulary;
identify a second translation function for the exercise machine;
translating the health related instruction in the unified vocabulary into a health related instruction translated for the exercise machine using the second translation function; and
providing, to the exercise machine, the health related instruction translated for the exercise machine.

10. The method of claim 1, comprising:
receiving, by the server, additional heart rate information of the user sensed by the wearable device of the multiple devices while the user is performing the long aerobic physical activity with the exercise machine; and
in response to receiving the additional heart rate information of the user sensed by the wearable device of the multiple devices while the user is performing the long aerobic physical activity with the exercise machine, providing, by the server to the exercise machine, a second health related instruction that triggers the exercise machine to perform a second physical action that makes a different long aerobic activity available to the user.

11. A system comprising:
one or more computers and one or more storage devices storing instructions that are operable, when executed by the one or more computers, to cause the one or more computers to perform operations comprising:
receiving, at a server of a system that includes (i) the server and (ii) a set of multiple devices that include a wearable device and an exercise machine, device capability information for each device in the set of multiple devices, where the device capability information from each device describes capabilities of the device and the exercise machine is configured to be triggerable by the server to perform a physical action that makes a long aerobic physical activity available to the user;

receiving, by the server, an indication of a health goal of a user;

receiving, by the server, heart rate information of the user sensed by the wearable device of the multiple devices;

determining, by the server based on the heart rate information sensed by the wearable sensor and the health goal of the user, to provide the long aerobic physical activity for the user to perform instead of to provide a short strength related physical activity for the user to perform;

determining, by the server, from the device capability information from the exercise machine that the long aerobic physical activity is available through the exercise device with performance of a physical action by the exercise machine;

in response to determining from the device capability information from the exercise machine that the long aerobic physical activity is available through the exercise machine with performance of the physical action by the exercise machine, generating, by the server, a health related instruction that triggers the exercise machine of the multiple devices to perform the physical action that makes the long aerobic physical activity available to the user;

receiving, by the server, an indication that the user has turned on the exercise machine; and in response to receiving the indication that the user has turned on the exercise machine, providing, by the server to the exercise machine, the health related instruction that triggers the exercise machine to perform the physical action that makes the long aerobic physical activity available to the user.

12. The system of claim 11, wherein the health related instruction additionally causes the exercise machine to display a recommendation of a particular exercise for the user.

13. The system of claim 11, wherein health related instruction additionally causes the exercise machine to begin monitoring particular health information of the user.

14. The system of claim 11, wherein receiving an indication of a health goal of a user comprises:
receiving the indication of the health goal of the user from a health provider device.

15. The system of claim 11, wherein generating, a health related instruction that triggers the exercise machine of the multiple devices to perform the physical action that makes the long aerobic physical activity available to the user comprises:
determining a health model that matches the health goal of the user;
identifying one or more user behaviors based on the health model and the health information of the user;
selecting a user behavior that is enabled by a capability of the exercise machine indicated by the device capability information of the exercise machine; and
determining the health related instruction for the exercise machine based on the selected user behavior.

16. The system of claim 11, wherein receiving device capability information comprises:
providing a first request for capability information to the wearable device;
receiving device capability information from the wearable device in response to the first request;
providing a second request for capability information to the exercise machine; and
receiving device capability information from the exercise machine in response to the second request.

17. The system of claim 11, wherein the exercise machine comprises a treadmill, a row machine, or a stair climber device.

18. The system of claim 11, wherein the first type of physical activity comprises a long aerobic activity and the second activity comprises a short strength related activity.

19. The system of claim 11, wherein receiving device capability information comprises receiving, from a treadmill, an indication of a range of speeds that the treadmill is capable of operating between,
wherein generating a health related instruction that triggers the exercise machine of the multiple devices to perform a physical action comprises determining, based at least on (i) the health goal of the user, (ii) the range of speeds that the treadmill is capable of operating between, and (iii) the heart rate information sensed by the wearable device, a speed that the treadmill should operate at between the range of speeds that the treadmill is capable of operating between.

20. A non-transitory computer-readable medium storing software comprising instructions executable by one or more computers which, upon such execution, cause the one or more computers to perform operations comprising:
receiving, at a server of a system that includes (i) the server and (ii) a set of multiple devices that include a wearable device and an exercise machine, device capability information for each device in the set of multiple devices, where the device capability information from each device describes capabilities of the device and the exercise machine is configured to be triggerable by the server to perform a physical action that makes a long aerobic physical activity available to the user;
receiving, by the server, an indication of a health goal of a user;
receiving, by the server, heart rate information of the user sensed by the wearable device of the multiple devices;
determining, by the server based on the heart rate information sensed by the wearable sensor and the health goal of the user, to provide the long aerobic physical activity for the user to perform instead of to provide a short strength related physical activity for the user to perform;
determining, by the server, from the device capability information from the exercise machine that the long aerobic physical activity is available through the exercise device with performance of a physical action by the exercise machine;
in response to determining from the device capability information from the exercise machine that the long aerobic physical activity is available through the exercise machine with performance of the physical action by the exercise machine, generating, by the server, a health related instruction that triggers the exercise machine of the multiple devices to perform the physical action that makes the long aerobic physical activity available to the user;
receiving, by the server, an indication that the user has turned on the exercise machine; and
in response to receiving the indication that the user has turned on the exercise machine, providing, by the server to the exercise machine, the health related instruction that triggers the exercise machine to perform the physical action that makes the long aerobic physical activity available to the user.

* * * * *